United States Patent [19]
Hofmann et al.

[11] Patent Number: 5,817,630
[45] Date of Patent: Oct. 6, 1998

[54] GLUTATHIONE ANTIOXIDANT EYE DROPS

[75] Inventors: Robert F. Hofmann, Austin; Don J. Bottoni, Pflugerville, both of Tex.

[73] Assignee: Austin Nutriceutical Corporation, Austin, Tex.

[21] Appl. No.: 820,214

[22] Filed: Mar. 18, 1997

[51] Int. Cl.$^6$ .......................... A61K 37/00; A61K 31/19
[52] U.S. Cl. .............................. 514/18; 514/557; 514/912
[58] Field of Search ................................ 514/18, 557, 912

[56] References Cited

PUBLICATIONS

WPIDS 95–06599 (1990). Saldotava et al.

*Primary Examiner*—Zohreh Fay
*Attorney, Agent, or Firm*—Banner & Witcoff, Ltd.

[57] ABSTRACT

An eye drop composition and a method of using the composition to alleviate eye discomfort and for improving lens pliability.

23 Claims, No Drawings

GLUTATHIONE ANTIOXIDANT EYE DROPS

FIELD OF THE INVETION

The present invention relates to an eye drop composition and a method of using the composition to alleviate eye discomfort. The present invention further relates to a method for reversing effects due to hardening of the human lens and reduction of lens pliability.

BACKGROUND OF THE INVETON

There are many factors that will irritate the eye such as pollutants, wind, sun, allergies, and contact lenses. Eye drops have been used to alleviate such irritations. Typically, such eye drops are found in over-the-counter formulations.

The eye also faces other problems such as hardening of the human lens (nuclear sclerosis) and reduced lens pliability (presbyopia) which result in the need for bifocal lenses. Reduced lens pliability tends to increase with age and becomes more and more difficult to treat as aging increases.

It is believed that hardening of the lens is related to the deposition of heavy metals in the eye that form metalloperoxides, which crosslink collagen fibers, reducing pliability of the lens. Normally, the eye can flush out small amounts of such heavy metals through it's own glutathione and lipoic acid (di-sulfhydryl chelator) mechanism. However, environmental, dental, industrial, and smoking sources can combine to overload the glutathione and lipoic acid mechanism of metal clearance resulting in reduced accommodation and near acuity. Accommodation is the phenomenon of functional shift in ocular focusing components from distance to near vision. Acuity is the perception of clarity, contrast, and spatial resolution through a physiological optical system. For instance, smoking (cadmium aerosolization) and dental amalgam (mercury, nickel, and others) accelerate loss of accommodation and increase nuclear optical density.

While the problems of aging are persistent, there is a need for a soothing comfort drop that reduces or reverses hardening of the lens and decreases the effects of presbyopia.

SUMMARY OF THE INVENTION

The present invention is directed to an eye drop composition comprising:

an effective amount of a plurality of antioxidants, wherein the antioxidants comprise at least glutathione or a derivative thereof, and lipoic acid;

an effective amount of at least one heavy metal chelator;

an effective amount of at least one oxygenating agent;

an effective amount of at least one trace element enzyme cofactor; and an effective amount of a penetrant.

The present invention is also directed to a method of relieving discomfort of an eye comprising adding to the eye an effective amount of the eye drop composition.

In addition, the present invention directed to a method for improving ocular lens pliability comprising adding to the eye an effective amount of the eye composition.

Other features and advantages of the present invention will become apparent to those skilled in the art from the following detailed description. It is to be understood, however, that the detailed description and specific examples, while indicating preferred embodiments of the present invention, are given by way of illustration and not limitation. Changes and modifications within the scope of the present invention may be made without departing from the spirit thereof, and the invention includes all such modifications.

DETAILED DESCRIPTION OF THE PREFERRED EMBODIMENTS

The present invention is directed to a soothing eye drop that, after administration, will comfort the eye by relieving dryness, itching, and burning. The composition will also protect the eye from pollution, and in particular heavy metals. The present invention is further directed to a method for slowing down or even reversing the hardening of the nucleus of the eye lens and the reduction of pliability of the eye lens.

The composition of the present invention contains an effective amount of a plurality of antioxidants including at least glutathione or a derivative thereof, and lipoic acid. The composition of the present invention includes effective amounts of at least one heavy metal chelator; at least one oxygenating agent, at least one trace element enzyme cofactor, and a penetrant. It was discovered that this combination has many benefits. For example, the combination of the heavy metal chelator and the antioxidants eliminates heavy metal binding and improves lens pliability.

Glutathione is available in many forms which are suitable for the present composition such as reduced L-Glutathione, and glutathione disulfide. The preferred form of glutathione is reduced L-Glutathione. The glutathione is preferably added in an amount of about 0.1 to 0.5 wt% based on the total weight of the solution, more preferably about 0.25 wt%.

The lipoic acid is preferably added in an amount of about 0.05 to 0.2 wt% based on the total weight of the solution, more preferably about 0.1 wt%. The lipoic acid may be solubilized by placing the lipoic acid in a small amount of water and then adding 30% sodium hydroxide by the drop until the lipoic acid is solubilized as sodium lipoate.

The heavy metal chelator is preferably added in an amount of about 0.05 to 0.5 wt% based on the total weight of the solution, more preferably about 0.1%. The heavy metal chelator may be any suitable chelator such as ethylenediamine tetraacetate (EDTA), cyclohexanediamine tetraacetate (CDTA), hydroxyethylethylenediamine triacetate (HEDTA), diethylenetriamine pentaacetate (DTPA), 1,2-diaminocyclohexane tetraacetate or hexametaphosphate. Other metal chelating agents include dimercaptopropane sulfonic acid (DMPS), or dimercaptosuccinic acid (DMSA). These agents are preferably employed as a ophthalmically acceptable salt, typically a sodium salt such as disodium EDTA, trisodium HEDTA, sodium hexametaphosphate, and the like. The chelating agent is most preferably EDTA.

In addition to the antioxidants glutathione and lipoic acid, at least one additional antioxidant may be added to the composition. Suitable antioxidants include vitamin E in a soluble form such as TROLOX-C, and vitamin C such as ascorbic acid. Vitamin E can work synergistically with vitamin C in protecting vital cell function from normal oxidants. The antioxidants are added in effective amount to scavenge free radicals and other oxidants, bind heavy metals, and prevent cross linking of the collagen fibers. The additional antioxidants are added in amounts effective as antioxidants, for example in cumulative amounts of 0.05 to 0.04 wt%.

Vitamin E is preferably added in amount of about 0.05 to 0.2 wt% based on the total weight of the solution, more preferably about 0.1 wt%. Vitamin E may be solubilized with DMSO, or other suitable penetrant, prior to addition to the remainder of the composition.

Vitamin C in the form of ascorbic acid, or any of its physiological salt ascorbates such as sodium ascorbate, is preferably added in an amount of about 0.05 to 0.2 wt% based on the total weight of the solution, more preferably about 0.1 wt%.

Any suitable penetrant or solubilizer may be used such as DMSO or derivatives thereof ($DMSO_2$, etc.). The penetrant is added in an effective amount, preferably about 0.05 to 0.2 wt% based on the total weight of the solution, more preferably about 0.1 wt%.

Any suitable oxygenating agents may be employed in the present invention such as germanium sesquioxide. The oxygenating agent is added in an effective amount, preferably about 0.05 to 0.2 wt% based on the total weight of the solution, more preferably about 0.1 wt%.

Preferably an essential amino acid chelator, bioflavonoid, porphyrin, or pycnogenol is added to the composition. Amino acid chelators include L-taurine, cysteine, glycine and methionine, preferably L-taurine. The amino acid chelator, bioflavonoid, porphyrin, or pycnogenol is added in an amount of about 0.05 to 0.25 wt% based on the total weight of the solution, more preferably about 0.1 wt%.

The trace element enzyme cofactor metabolizes metalloenzymes and antioxidant enzymes. This cofactor is typically a polyvalent cation such as calcium, magnesium, manganese, iron, chromium, copper, selenium, or zinc, in the form of a salt. Zinc chloride or zinc sulfate are the preferred cofactors. The trace element enzyme is added to the composition in an effective amount, for example, about 0.005 to 0.2 wt% based on the total weight of the solution, preferably about 0.01 wt%.

The ingredients are combined and diluted with a suitable diluent. The diluent is preferably a 1.0 to 1.4% polyvinyl alcohol solution to achieve a final solution quantity of 15 ccs. (Q.S. to 15 ccs). Polyvinyl alcohol is the diluent of choice because it increases solution viscosity and adherence to the corneal surface. Other diluents that could be utilized are solutions containing methyl cellulose derivatives and/or hyaluronic acid derivatives.

The pH is adjusted to about 7.0 to 7.4 using a suitable base such as sodium hydroxide solution. The composition should be refrigerated and protected from light. The shelf life is about 3 to 6 months.

The drops are added to the eyes as needed in an amount effective to soothe the eyes. Typical dosage amounts include 1 to 2 drops preferably 2 to 4 times daily. If the drops are used to reverse the effects of lens hardening, then the term of utilization is indefinite. The drops are best started early in the degenerative process and used continuously without the presence of heavy metal systemic toxins such as mercury, cadmium, aluminum, nickel, palladium, beryllium, or arsenic. In addition to the treatment with the drops, it is advisable to avoid or eliminate toxic metal sources such as dental amalgams, smoking, aluminum cookware, cosmetics, medications, industrial sources, and polluted tapwater.

Other ingredients may be added to the eye drop composition such as surfactants, tonicity adjusting agents, buffering agents, viscosity modifying agents, and disinfecting agents. These ingredients are added in amounts effective to perform their function and are well within the skill of the art.

EXAMPLES

Example 1

An ophthalmic composition was prepared with the following formulation:

| INGREDIENT | %/wt. |
| --- | --- |
| L-Glutathione Reduced | 0.25 |
| Ascorbic Acid | 0.1 |
| Lipoic Acid | 0.1 |
| Germanium Sesquioxide | 0.1 |
| L-Taurine | 0.1 |
| E.D.T.A. | 0.1 |
| Vitamin E (TROLOX-C) | 0.1 |
| Zinc Chloride | 0.01 |
| D.M.S.O. | 0.1 |

This composition was first administered to patients through a pharmacy without disclosure of the contents. The results provided an effective and comfortable eye drop having excellent adherence to the cornea and the same efficacy as obtained for example 2 below.

Example 2

A transcorneal infusion of natural chelating agents and oxygenating agent combined with an effective penetrant was tested for its effect upon accommodation, lens clarity, and corneal integrity. The composition of the drops used in this clinical trial is similar to that disclosed in Example 1 except for the nature of the solubilized form of Vitamin E (TROLOX-C) and the use of balanced salt solution instead of polyvinyl alcohol. The active ingredients, chelators, oxygenating agent and penetrant were the same in both compositions.

Parameters:

100 eyes in 50 patients (25 female/25 male) aged 42 to 55 were administered the drops 3 times per day over a six month period. The drops were contained in coded labeled brown dropper bottles and the contents were not revealed to the patient. Each patient was given two bottles; one a placebo of normal saline (control) and one with the formula for use each in one eye only in a double masked manner, and were asked to place one set in specific eye and not to crossover. Accommodation was measured initially and monthly by Prentice ruler over full manifest distance spectacle correction. Lens clarity was assessed objectively by Interzeag Opacity Lensmeter at the same visits. Slit lamp examination and distance manifest refraction were performed monthly. Note was made of smoking and dental amalgam history. Any patients with ocular disease, strabismus or previous globe trauma were not accepted into the study. The presence of a posterior vitreous separation or manifest refractive error over 2 diopters prevented inclusion of the patient in the study.

Dropout:

6 patients (4 male/2 female) left the study. 4 did not maintain interest. 2 moved from the area. No patients stopped due to discomfort or adverse reaction.

Baseline:

Amplitude of accommodation ranged from 1.0 to 4.8 diopters with a mean of 2.7 diopters. No difference based upon sex was delineated. Patients over 50 y/o averaged 1.6 diopters compared to those under 50 y/o at 3.0 diopters. Smokers (18 patients) averaged 0.87 diopters less amplitude than non-smokers in their age group. Dental amalgam presence influenced an age matched reduction of 0.82 diopters. Amalgam plus smoking caused an age matched reduction of 1.36 diopters.

Lens density ranged from 10.2 to 16.5 DB. (mean 12.6 DB.) Patients in their fifties had density figures of 13.9 to 16.5 (mean 14.7 DB.). Patients in their forties had densities of 10.2 to 14.3 (mean 12.88 DB.). Smoking increased lens opacity by 1.5 DB., amalgams by 1.3 DB. and combination by 2.1 DB. mean in each age group. The sex of the patient had no influence over lens density.

Interim (2 months):

No control eye showed significant change in any parameter. The over fifty group also showed no significant shift in study parameters. Smokers and amalgam patients showed no improvement. The under 50 group showed a mean improvement of 0.75 diopters accommodation (range 0.0 to 1.75) and an opacity reduction mean of 0.42 DB.

Final (6 months):

Control eyes lost a mean of 0.48 (range 0.1 to 1.65) diopters accommodation and increased lens density mean of 0.65 (range 0.0 to 1.3) DB. Smokers and amalgam patient controls lost a mean of 0.85 diopters accommodation and increased lens density by a mean of 0.96 DB. There was no significant difference between each age group controls.

Treated eyes over 50 y/o improved accommodation by a mean of 2.8 diopters (range 0.5 to 3.4). Treated eyes less than 50 y/o improved accommodation by a mean of 3.6 diopters (range 1.5 to 5.0). All treated lens densities lessened by 1.6 (range 0.4 to 2.6 DB.). Smoking and amalgam presence reduced the mean improvement in each age group by 35% for accommodation and worsened lens density by 25%.

Problems:

Except for minor burning sensation upon instillation, no pathological changes to the cornea occurred in any patient. Due to a lack of preservative, the drops required refrigeration. Those not refrigerated turned yellow, but that did not seem to increase intolerance or decrease efficacy. The color change of the aged, non-preserved, non-refrigerated solution was due to oxidation of DMSO to $DMSO_2$. This color change did not reduce clinical efficacy or tolerance.

Conclusion:

Topical chelators with DMSO penetrant drops over a six month period (no less than 3 months) in the short term significantly retard or reverse the process of presbyopia (hardening of the lens) and lens nuclear sclerosis in patients 42 to 55 y/o. No adverse pathological changes or reduction in acuity occurred in this study.

We claim:

1. An eye drop composition comprising
   an effective amount of a plurality of antioxidants, wherein the antioxidants comprise at least glutathione or a derivative thereof, and lipoic acid;
   an effective amount of at least one heavy metal chelator;
   an effective amount of at least one oxygenating agent;
   an effective amount of at least one trace element enzyme cofactor; and
   an effective amount of a penetrant.

2. The composition of claim 1 wherein the heavy metal chelator is E.D.T.A. or a derivative thereof.

3. The composition of claim 1 wherein the penetrant is DMSO or $DMSO_2$.

4. The composition of claim 1 further comprising at least one additional antioxidant.

5. The composition of claim 4 wherein the additional antioxidant is vitamin E, vitamin C, or both.

6. The composition of claim 1 wherein the oxygenating agent is germanium sesquioxide.

7. The composition of claim 1 further comprising at least one chelating essential amino acid, bioflavonoid, porphyrin, or pycnogenol.

8. The composition of claim 7 further comprising an essential amino acid.

9. The composition of claim 8 wherein the essential amino acid is L-Taurine.

10. The composition of claim 1 wherein the trace element enzyme cofactor is zinc chloride or zinc sulfate.

11. An eye drop composition comprising:
    0.1–0.5 wt% L-Glutathione Reduced;
    0.05–0.2 wt% lipoic acid;
    0.05–0.2 wt% germanium sesquioxide;
    0.05–0.25 wt% L-Taurine;
    0.05–0.5 wt% E.D.T.A.;
    0.05–0.25 wt% zinc chloride;
    0.05–0.2 wt% DMSO; and
    a suitable diluent.

12. The composition of claim 11 further comprising:
    0.05–0.2 wt% ascorbic acid; and
    0.05–0.2 wt% Vitamin E.

13. An eye drop composition comprising:
    0.25 wt% L-Glutathione Reduced;
    0.1 wt% ascorbic acid;
    0.1 wt% lipoic acid;
    0.1 wt% germanium sesquioxide;
    0.1 wt% L-Taurine;
    0.1 wt% E.D.T.A.;
    0.1 wt% Vitamin E;
    0.01 wt% zinc chloride;
    0.1% wt% DMSO; and
    a suitable diluent.

14. A method of relieving discomfort of an eye comprising adding to the eye a composition comprising:
    an effective amount of a plurality of antioxidants, wherein the antioxidants comprise at least glutathione or a derivative thereof, and lipoic acid;
    an effective amount of at least one heavy metal chelator;
    an effective amount of at least one oxygenating agent;
    an effective amount of at least one trace element enzyme cofactor; and
    an effective amount of a penetrant.

15. The method of claim 14 further comprising vitamin E, vitamin C, or both.

16. The method of claim 14 further comprising at least one chelating essential amino acid, bioflavonoid, porphyrin, or pycnogenol.

17. The method of claim 16 further comprising the essential amino acid L-Taurine.

18. The method of claim 14 wherein the trace element enzyme cofactor is zinc chloride or zinc sulfate.

19. A method for improving ocular lens pliability and accommodation comprising adding to the eye an effective amount of a composition comprising
    an effective amount of a plurality of antioxidants, wherein the antioxidants comprise at least glutathione or a derivative thereof, and lipoic acid;
    an effective amount of at least one heavy metal chelator;
    an effective amount of at least one oxygenating agent;
    an effective amount of at least one trace element enzyme cofactor; and
    an effective amount of a penetrant.

20. The method of claim 19 further comprising vitamin E, vitamin C, or both.

21. The method of claim 19 further comprising at least one chelating essential amino acid, bioflavonoid, porphyrin, or pycnogenol.

22. The method of claim 21 further comprising the essential amino acid L-Taurine.

23. The method of claim 19 wherein the trace element enzyme cofactor is zinc chloride or zinc sulfate.

* * * * *